United States Patent [19]

Yang et al.

[11] Patent Number: 5,340,904

[45] Date of Patent: Aug. 23, 1994

[54] BIS(4-AMINOPHENOXY)NAPHTHALENE AND ITS POLYMERS

[75] Inventors: Chin-Ping Yang; Wen-Tung Chen, both of Taipei, Taiwan

[73] Assignee: National Science Council, Taipei, Taiwan

[21] Appl. No.: 997,094

[22] Filed: Dec. 29, 1992

[51] Int. Cl.[5] .................... C08G 73/10; C07C 217/90
[52] U.S. Cl. .................... 528/185; 528/170; 528/171; 528/172; 528/173; 528/174; 528/176; 528/188; 528/220; 528/229; 528/350; 528/353; 564/428
[58] Field of Search .............. 528/185, 188, 220, 229, 528/350, 353, 170, 171, 172, 173, 174, 176; 564/428

[56] References Cited

U.S. PATENT DOCUMENTS 5,076,817  12/1991  Hayes ........................... 55/16

FOREIGN PATENT DOCUMENTS 9212120  7/1992  World Int. Prop. O. .

OTHER PUBLICATIONS

CA 116(14):130819y, Apr. 6, 1992, "Aromatic polyamide membranes for gas separation", Hayes.
CA 117(22):214097v, Nov. 30, 1992, "Heat-resistant aromatic polyimide membranes for gas separation", Hayes.
CA 117(19):191511j, Nov. 9, 1992, "Preparation of bis-(aminophenoxy) naphthalenes and bis(nitrophenoxy)-naphthalenes", Renner.

*Primary Examiner*—John Kight, III
*Assistant Examiner*—P. Hampton-Hightower
*Attorney, Agent, or Firm*—Brumbaugh, Graves, Donohue & Raymond

[57] ABSTRACT

A compound or polymer having a bis(phenoxy)naphthalene structure, a high molecular weight, and very good mechanical performance and heat-resistivity is provided. The polymer can be polyamides, polyimides or poly(amide-imide)s and can have a basic structure of

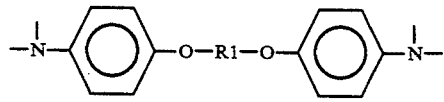

wherein R1 is a naphthalene ring.

3 Claims, No Drawings

BIS(4-AMINOPHENOXY)NAPHTHALENE AND ITS POLYMERS

BACKGROUND OF THE INVENTION

The present invention relates to a compound, and also to a polymer polymerized therefrom.

Naphthalene, which is a well-known material in the early time, is a by-product when the coke is refined from the coal. It is widely used in the insectifuge for the family clothing and the intermediate of the dyestuff. Owing to the development of the steel industry, there is much naphthalene produced. Therefore, it would be advantageous if we can exploit a new use therefor.

The naphthalene and the benzene both are aromatic compounds. The naphthalene ring being condensated from the benzene has its own property. In some special industry of late years, there is an urgent need for a high performance polymer material which can be provided by an aromatic polymer having a good heat-resistivity and a high rigidity. Such polymer material includes the aromatic polyether-sulfone, polyetherketone, liquid crystal polyester, amorphous polyester, polyamides, polyimides... etc. Most of such high performance polymer materials contain the benzene ring structure. So far as the molecular structure is concerned, a polymer having a naphthalene ring should have better heat-resistivity and rigidity. In the high performance polymers having the naphthalene ring, till now only the 2,6-naphthalenedicarboxylic acid or 2,6-dihydroxynaphthalene is known to be capable of being used to prepare the liquid crystal polymers and there are few reports for the successful development with other material. Although there is the commercial 1,5-naphthalene diamine, the polymer derived from such diamine is of no practical value because of its less favorable performance.

Generally monomers for polycondensation are prepared to be two functional group compounds. At present it is easier to get the dihydroxynaphthalene than the naphthalene diamine from naphthalene. Therefore there have been many kinds of dihydroxynaphthalenes in the market. Because a polymer containing the aromatic-ether unit has good mechanical properties and processability and the diamine has a wide application in the polycondensation reaction, there are many kinds of polycondensated polymers including polyamides, polyimides and copoly(amide-imide)s prepared from the bis(4-aminophenoxy)naphthalene derived from the commercial dihydroxynaphthalene. It is found that such polymer not only has a high molecular weight, but also has better mechanical properties and heat-resistivity to meet the requirements for high performance. As to the past research for the bis(4aminophenoxy)naphthalene, only in 1989 the Japanese Asia Fuel Association bringing up an invention for the disulfone-containing dianhydride for preparing the soluble polyimides mentioned that the 2,6-bis(4-aminophenoxy)naphthalene can be as the diamine, but did not mention any preparing method or physical property data thereof. As to 2,3-, 2,7-, 1,5-, 1,6, or 1,7-bis(4-aminophenoxy)naphthalene, there is no technical literature making any mention of those monomers. Thus, the bis(phenoxy)naphthalene-containing diamines and their related polymers should be novel monomers and materials respectively.

SUMMARY OF THE INVENTION

It is therefore an object of the present invention to provide a polymer having good heat-resistivity and/or mechanical strength and/or soluble processability.

The present invention provides a series of polymers including polyamides, polyimides and poly(amide-imide)s capable of being polycondensated from bis(p-aminophenoxy)naphthalenes and various dicarboxylic acids, various aromatic dianhydrides, trimellitic anhydride and various dicarboxylic acids having the imide ring.

According to the present invention, a bis(4aminophenoxy)naphthalene has the following structure:

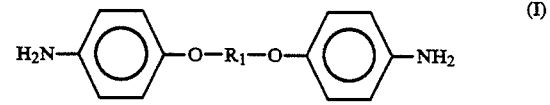

(I)

wherein R can be one of the following structures:

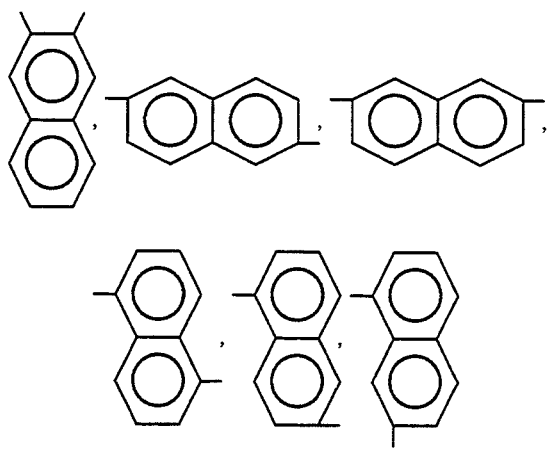

If we allow such bis(4-aminophenoxy)naphthalene to react with the dicarboxylic acid (or dianhydride), we can obtain polycondensated polymers including polyamides, polyimides, and poly(amide-imide)s having the following general formula:

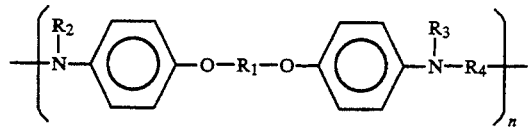

wherein n is an integer ranged from 5-500, R1 is the same to the above, and (i) if R2 and R3 both are protons (H), then R4 is:

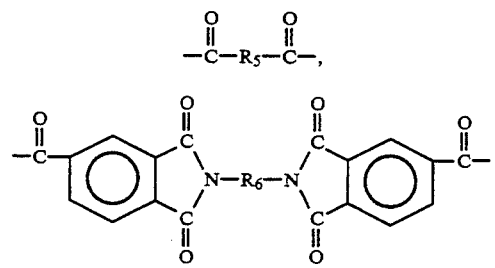

-continued
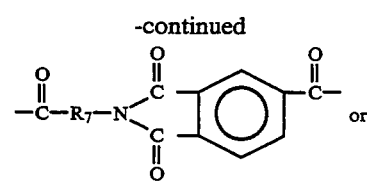
or
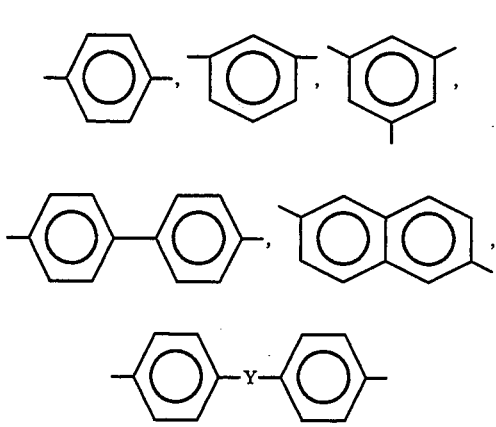
R5 is
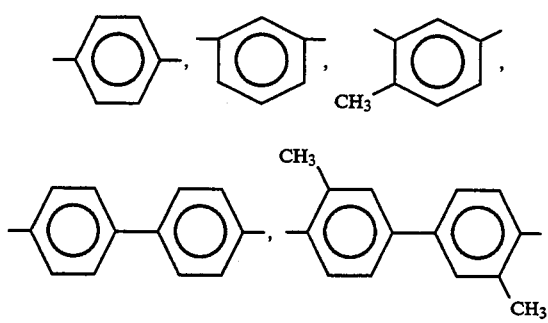
(Y=SO₂, (CH₃)₂—C,(CF₃)₂—C, the aliphatic ring or the aliphatic chain—(CH₂)m—)
R6 is
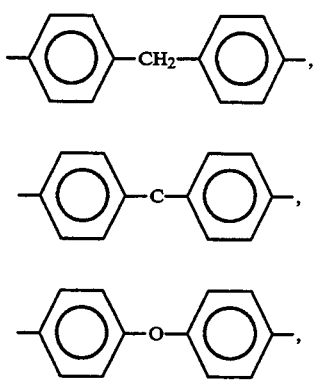
-continued
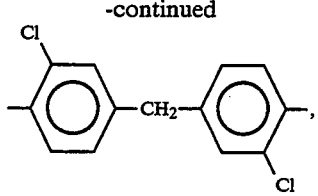
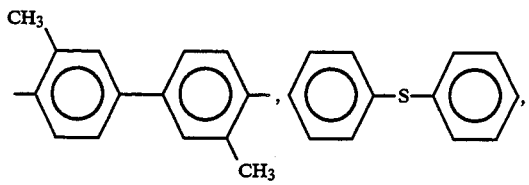
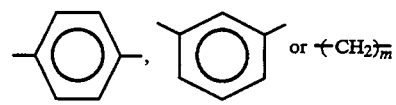
R7 is
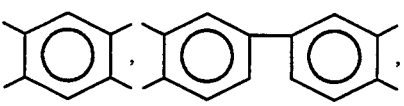
(m = 1, 2, 3, 4, 5, 10, 11);
R8 is
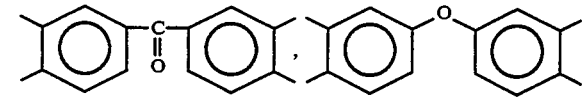
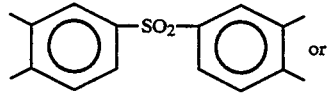 or

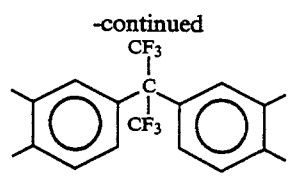

(ii) if R2 and R3 both are not proton (H), then R8 is the same to the above, R2 represents a single bond, and R3 and R4 cooperatively have the following structure:

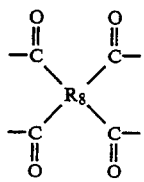

The present invention may better be understood through the following description.

DETAILED DESCRIPTION OF THE PREFERRED EMBODIMENT

The di(ether amine) having the naphthalene unit can be condensated from and then reduced by hydrogenation the dihydroxynaphthalene and the p-chloronitrobenzene. If we use the 2,3-dihydroxynaphthalene as an example, the chemical reaction formula will be as follow:

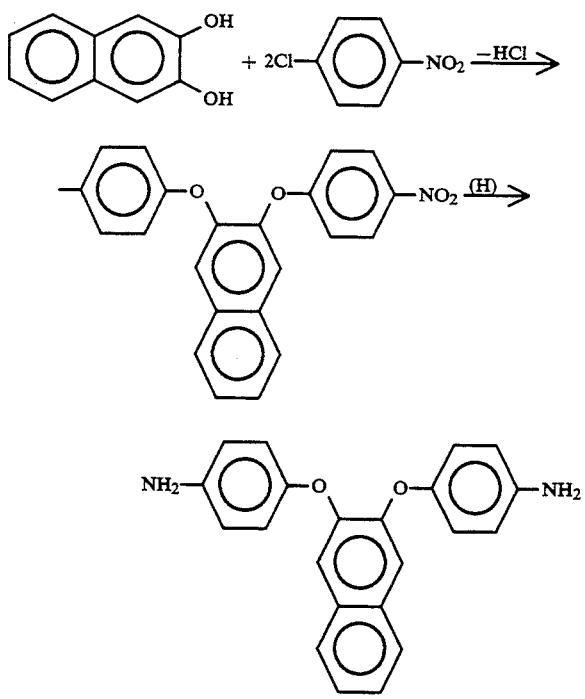

The Condensation reaction for removing HCl can be completed by a heating reaction in the aprotic solvent (DMF, DMSO, or NMP, for example) being added therein the potassium carbonate. The reduction by hydrogenation can be performed by passing the hydrogen into an adequate solvent, e.g. DMF under the existence of the metallic reduction catalyst (e.g. Pd/C, Raney Ni). Certainly, the hydrazine/Pd-c method can be conveniently used to prepare the compound shown in formula I.

Since 2,3-, 2,7-, 1,5-, 1,6- or 1,7- bis(4-aminophenoxy)-naphthalene is a kind of new compound, there is no report till now for the preparation and the application thereof. Although 2,6- isomer was once mentioned in 1989 to be served as the constituent for polymers, there is no any data for such diamine, including the melting point, the preparing method...etc.

The present synthesized diamines including 1) 2,3-bis(4-aminophenoxy) naphthalene, 2) 2,6-bis(4-aminophenoxy) naphthalene, 3) 2,7-bis(4-aminophenoxy)-naphthalene, 4)1,5-bis (4-aminophenoxy)naphthalene, 5) 1,6-(4-aminphenoxy) naphthalene, and 6)1,7-bis(4-aminophenoxy)naphthalene, respectively have the yield (based on dihydroxynaphthalene), the melting point, elemental analyses, and the structure as follows:

| Di-amine | Yield (%) | MP(°C.) | | Elementary Analytic Values | | |
|---|---|---|---|---|---|---|
| | | | | C | H | N |
| 1) | 84–95 | 176–177 | Calculated values: | 77.19 | 5.26 | 8.18 |
| | | | Found values: | 77.06 | 5.46 | 8.08 |
| 2) | 72–85 | 199–200 | Calculated values: | 77.19 | 5.26 | 8.18 |
| | | | Found values: | 77.04 | 5.38 | 8.14 |
| 3) | 75–85 | 166–167 | Calculated values: | 77.19 | 5.26 | 8.18 |
| | | | Found values: | 77.04 | 5.19 | 8.25 |
| 4) | 72–82 | 170–171 | Calculated values: | 77.19 | 5.26 | 8.18 |
| | | | Found values: | 77.10 | 5.14 | 8.05 |
| 5) | 78–89 | 162–163 | Calculated values: | 77.19 | 5.26 | 8.18 |
| | | | Found values: | 77.05 | 5.30 | 8.05 |
| 6) | 70–81 | 133–135 | Calculated values: | 77.19 | 5.26 | 8.18 |
| | | | Found values: | 77.09 | 5.37 | 8.17 |

Diamine structure

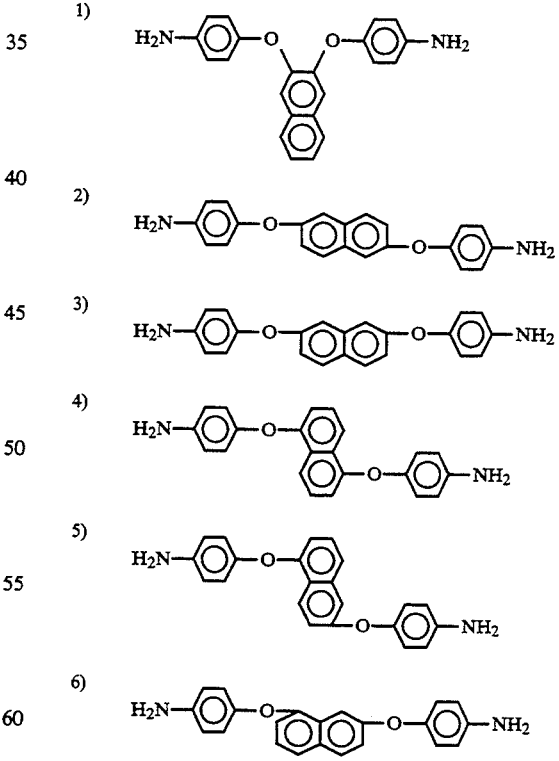

Polymers according to the present invention capable of being polymerized from the present bis(4-aminophenoxy) naphthalene include polyamides, polyimides and copoly(amideimide)s, the preparing methods of which are respectively described in the following. The polyamide contains a bisoxynaphthalene chain section in the main chain. It can be synthesized by polycondensating one of various kinds of di(ether amine)s having the naphthalene ring and the dicarboxylic acid or the activated dicarboxylic acid. When directly reacting with the dicarboxylic acid, we may use a condensing agent to carry out the polycondensation. One of the most suitable condensing agents is the triphenyl phosphite-pyridine system. When reacting with the activated dicarboxylic acid such as the diacid chloride, we may use the aprotic solvent of the amide type such as DMAc or NHP to make direct reaction for the manufacture of polyamides. The chemical reaction equation is as follows:

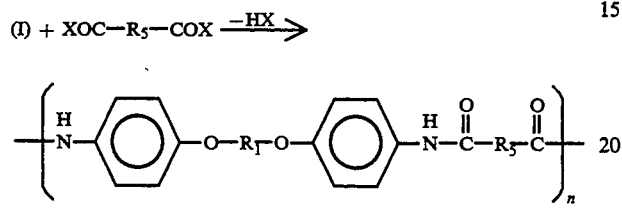

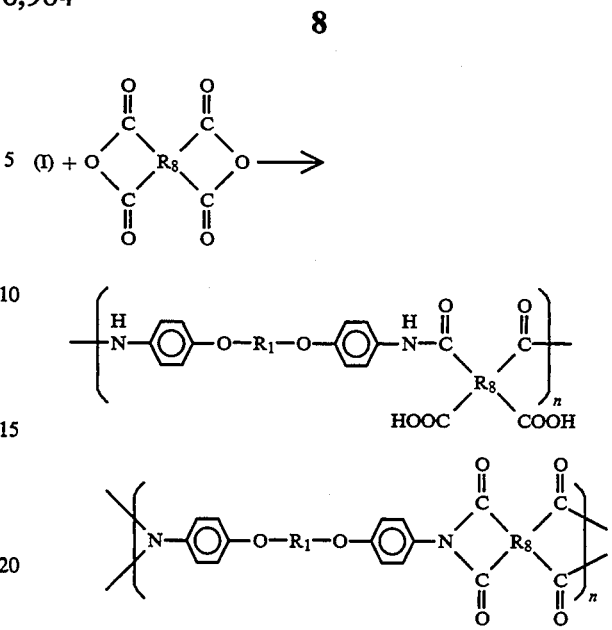

wherein X represents OH or Cl, and R1 and R5 are as described in the Summary.

The polyimide containing a bis(oxy)naphthalene chain section can be prepared by the polyaddition of the bis(4aminophenoxy)naphthalene and the dianhydride in the proper organic solvent to form the poly(amic acid). Then the poly(amic acid) is heated or is added with a dehydrating agent to be polymerized into the polyimide. The chemical reaction equation is as follows:

wherein R1 and R8 are as described in the Summary.

The copoly(amide-imide) is related to the trimellitic anhydride(TMA) and can be condensated from the 1 mole diamine and 2 mole TMA to obtain the diimide-diacid which is then polycondensated with the bis(4-aminophenoxy)naphthalene into the copoly(amide-imide) of the alternating type. The chemical reaction equations are as follows:

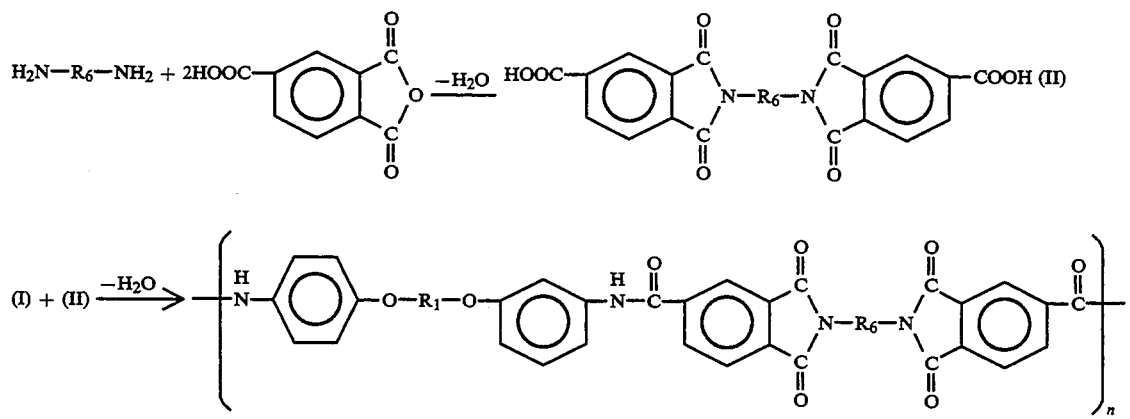

wherein R1 and R6 are as described in the Summary.

The copoly(amide-imide) can be polycondensated from the diamine of the bisoxynaphthalene and the diimide-diacid synthesized or condensated from the trimellitic trianhydride (TMA) and the amino acid. The reaction equations are as follows:

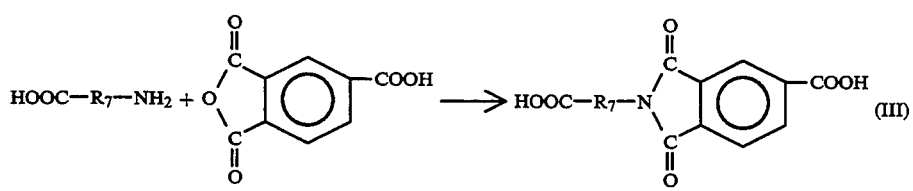

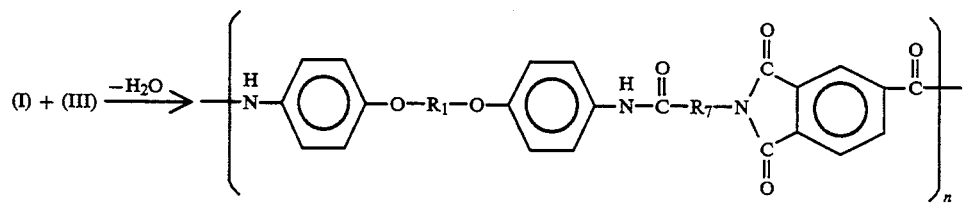

wherein R1 and R7 are as described in the Summary.

Alternatively, the copoly(amide-imide) can be polycondensated in the aprotic solution from the diamine having the bisoxynaphthalene unit and one of the family of diimide-diacids which can be condensated from one mole dianhydride and two moles amino acid. The chemical reaction equations therefor are as follows:

Molecular structure:

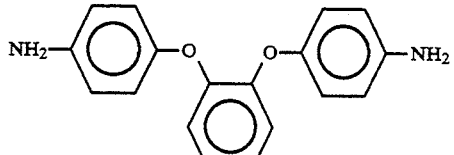

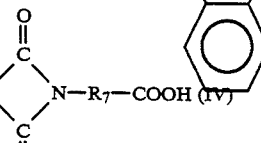

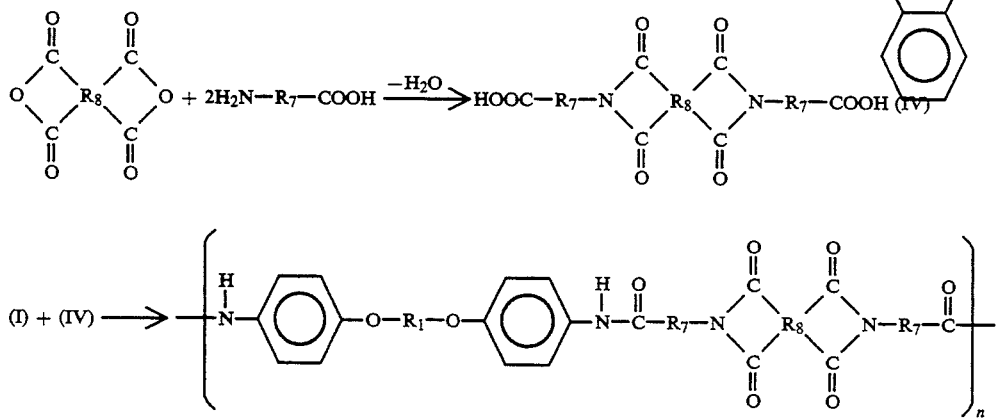

wherein R1 and R7 are as described in the Summary.
Some exemplary detailed preparing procedures of the compound and the polymers according to the present invention are described hereinafter. The preparation of the diamine-2, 3-bis(4-aminophenoxy)naphthalene is as follows:

In the 500 ml flask, there are added 40 g 2,3dihydroxynaphthalene, 83 g p-chloronitrobenzene, 79 g anhydrous potassium carbonate, and 300 ml DMF, all of which are subject to an oil bath at 160° C. to reflux for 8 hours. After the reaction is completed and cooled to the room temperature, the mixture was then poured into 500 ml methyl alcohol-water mixture (vol. ratio 1:1). The precipitate was collected by filtration. Then we can obtain 94 g 2,3-bis(4 nitrophenoxy)naphthalene (93%) from which we can have it recrystallized by the glacial acetic acid to obtain 82 g yellow needlelike material having a melting point of 199°-200° C.

In the 1000 ml flask, there are added therein 61 g 2,3-bis(4-nitrophenoxy)naphthalene, 0.3 g Pd/C and 400 ml ethyl alcohol, and gradually dropped therein 150 ml hydrazine at 80° C. to react for four hours. Thereafter, if we filter the solution in the flask when hot, we get 43 g (84%) white slices of di(ether amine) having a melting point of 176°-177° C.

Elementary analysis:
Calculated values C: 77.19%, H: 5.26%, N: 8.18% ;
Analytical values C: 77.06%, H: 5.46%, N: 8.08%.

Using similar procedures, we can get other kinds of bis(4 aminophenoxy)naphthalenes as follows:
2,6-bis(4-aminophenoxy)naphthalene having a yield of 72-85% and a melting point of 199°-200° C.;
2,7-bis(4-aminophenoxy)naphthalene having a yield of 75-85% and a melting point of 166°-167° C.;
1,5-bis(4-aminophenoxy)naphthalene having a yield of 72-82% and a melting point of 170°-171° C.;
1,6-bis(4-aminophenoxy)naphthalene having a yield of 78-89% and a melting point of 162°-163° C.;
1,7-bis(4-aminophenoxy)naphthalene having a yield of 70-81% and a melting point of 133°-135° C.

The polyamide (2,3) can be prepared as follows:
In 50 ml flask, we put 0.427 g(1.25 mmole) 2,3-bis(4-aminophenoxy)naphthalene, 0.27 g(1.25 mmole) 2,6-naphthalene dicarboxylic acid, 0.2 g calcium chloride, and 4 ml N-methylpyrrolidone (NMP). Then, the flask is subject to an oil bath at 100° C. and allowed to stirredly react for 3 hours until the solution therein becomes a viscous liquid which is then poured into the stirred methyl alcohol to release fibroid polyamides. We dip the fibroid polyamides in the methyl alcohol for one night. Thereafter, if we wash by hot water and then bake the fibroid polyamides, we can get 0.653 g(100%) polyamide which, when measured in the dimethylacetamide (DMAc), has an inherent viscosity 1.15 dl/g (30° C). Elementary analysis values, the mechanical strength, the heat-resistivity and the molecular structure thereof are respectively as follows:

Elementary Analysis:($C_{34} H_{22} N_2O_4$) n
Caculated values C: 78.19% H: 4.24%, N: 5.36% ;
Analysized values C: 75.74%, H: 4.57%, N: 5.23% (with moisture absorption 3.3%);
Revised values C: 78.34%, H: 4.72%, N:5.41%.

Mechanical properties:

| Yield strength | Elongation at Break | Initial Modulus |
|---|---|---|
| 78 MPa | 6% | 1.8 GPa |

10% Weight Loss Temperature: In Nitrogen 538° C. and in air 496° C.
Molecular structure:

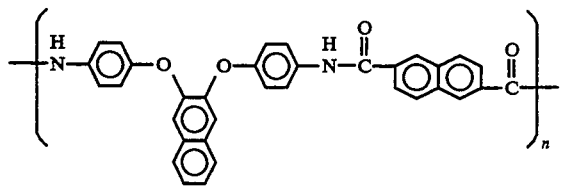

The preparing procedures of the polyamide (1,5) are as follows:

In the 50 ml flask, there are added therein 0.427 g(1.25 mmol) 1,5-bis (4-aminophenoxy)naphthalene, 0.2075 g (1.25 mmol) isophthalic acid, 0.18 g Calcium chloride, 2.5 ml NMP, 0.7 ml pyridine and 0.8 ml TPP. Then, following the heating reaction procedures for the preceding polyamide (2,3), we can obtain 0.59 g (99%) polyamide which exhibits an inherent viscosity 1.14 dl/g. Elementary Analysis values, the mechanical properties, the heat-resistivity and the molecular structure respectively as follows:

Elementary Analysis: ($C_{30} H_{20} N_2O_4$)n;
Calculated Values C: 76.26%, H: 4.69%, N: 5.92% ;
Analysized values C: 73.36%, H: 4.04%, N: 5.78%(with moisture absorption 3.67%);
Revised values C: 76.15%, H: 4.19%, N: 6.00% .

Mechanical Properties:

| Yield strength | Elongation at Break | Initial Modulus |
|---|---|---|
| 82 MPa | 9% | 2.0 GPa |

10% weight Loss Temperature: In Air 505° C. and In Nitrogen 510° C.
Molecular Structure:

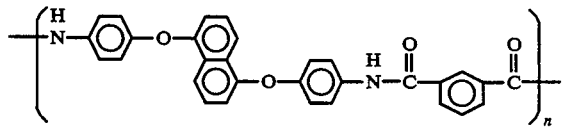

The preparing procedures for the polyimides (2,7) are as follows:

In 50 ml flask, we put 0.856 g (2.5 mmole) 2,7-bis(4-aminophenoxy) naphthalene, and add therein 13.5 ml anhydrous DMAc. After dissolved, cooled by the icy water, and air replaced, we totally put 0.545 g refined pyromellitic dianhydride (PMDA) in separate times within 30 minutes into the flask. Then, we stir the solution in the flask for 2 hours under the room temperature to grow up the poly(amic acid) which, when measured in 0.5 Sg/dl DMAc at 30° C., exhitits an inherent viscosity 1.94 dl/g. If we cast such poly(amic acid) on the clean glass plate being then put into an oven to be baked at 80° C. to form into the solid film, through evaporation of the solvent and then further baked in the oven at 110° C., 150° C., 180° C., 210° C., 230° C. and 250° C. respectively for 15 minutes, we can get the polyimide thin film which respectively has elementary analysis values, the mechanical strength, the heat-resistivity and molecular structure as follows:

Elementary analysis:($C_{22} H_{16} N_2O_6$)n;
Calculated Values: C: 73.28% H: 3 07% N: 5.34% ;
Analysized Values: C: 73.50%, H: 2.98%, N: 5.30%.

Mechanical Properties:

| Yield strength | Elongation at Break | Initial Modulus |
|---|---|---|
| 86 MPa | 7% | 1.92 GPa |

10% Weight Loss Temperature: In air 565° C. and in Nitrogen 573° C.
Molecular Structure:

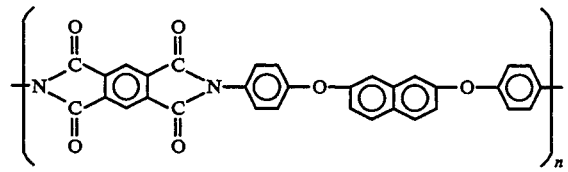

The polyimide (2,6) can be prepared as follows:

In 50 ml flask, we put 0.427 g(1.25 mmole)2,6-bis(4-aminophenoxy)naphthalene, and add 7.6 ml anhydrous DMAc. After dissolved, we put in the flask 0.367 g(1.25 mmlo) 3,3', 4,4'-biphenylene tetracarboxylic dianhydride in separate times within 30 minutes to stirredly react therein for 2 hours to get the poly(amic acid) exhibiting (in 0.5 Sg/dl DMAc at 30° C.) an inherent viscosity 0.86 dl/g. Then, following the baking proceduces for the above we can obtain the polyimide film which respectively has elementary analysis values the mechanical strength, the heat-resistivity and the molecular structure as follows:

Elementary analysis: ($C_{38} H_{20}N_2O_7$)n;
Calculated Values: C: 74.02%, H: 3.27%, N: 4.54%;
Analysized Values: C: 74.12%, H: 3.30%, N: 4.81%.

Mechnical Properties:

| Yield Strength | Elongation at Break | Initial Modulus |
|---|---|---|
| 122 MPa | 15% | 2.0 GPa |

10% Weight Loss Temperature: In air 570° C. and in Nitrogen 577° C.
Molecular Structure:

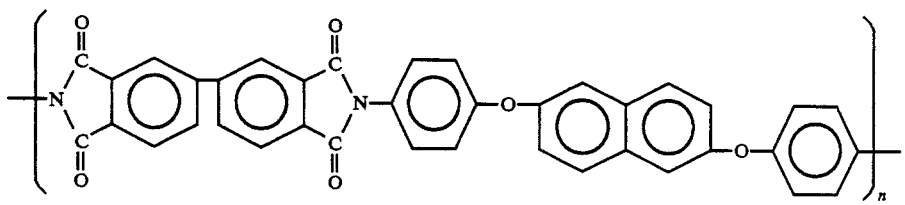

The copoly(amide-imide)(1,5) can be prepared as follows: With 0.01 mole(2.18 g) pyromellitic anhydride and 0.02 mole 4-aminobutanoic acid to be stirredly dissolved, heated and condensated in 30 mole anhydrous DMF, we can quantitatively prepare the N N'-bis(3-carboxypropyl)pyromellitimide. In 50 ml flask, we add 1.25 mmole N,N'-bis(3-carboxypropyl)pyromellitimide and 1.25 mmole 1,5-bis (4-aminophenoxy) naphthalene, 0.8 g calcium chloride, 5 ml NMP, 1.4 ml pyridine and 0.8 ml triphenyl phosphite (TPP). Then, the solution in the flask is subject to an oil bath at 100° C. and stirredly heated for 3 hours, and then poured into the methyl alcohol to precipitate fibroid polymers from which after alternately dipped in and washed with the methyl alcohol and hot water, we can get 0.917 g polymer exhibiting in DMAc an inherent viscosity 0.60 dl/g. The thin film casted from the DMAc has mechanical properties dimethyl formamide in a 300 ml flask at 40° C., we add in the solution in the flask 20 ml anhydrous toluene to be stirredly boiled azeotropically for 4 hours and add therein, after cooled, the methyl alocohol to quantitatively release a bis(trimellitimide) of the 1,3-bis(N,N-trimellitoyl)benzene. In 50 ml flask, there are added 0.57 g (1.25 mmole) such bis(trimellitimide), 0.427 g (1.25 mmole) 2.7-bis(4aminophenoxy)naphthalene, 0.8 g calcium chloride, 8 ml N-methyl-2-pyrrolidone(NMP), 1.6ml pyridine and 0.8ml triphenyl phosphite to stirredly react at 100° C. for 3 hours. Then, we pour the viscous solution into the stirred methyl alcohol to get fibroid polymers which, after fully washed by methyl alcohol and hot water and then dried, we can get 0.952 g polymer (yield 100%) which has an inherent viscosity 0.92 g dl/g and exhibits physical properties, after casted from DMAc into the thin film, as follows:

| Mechanical Properties: | | |
|---|---|---|
| Breaking Strength | Elongation at Break | Initial Modulus |
| 74 Mpa | 9% | 2.1 Gpa |

10% weight Loss Temperature: In Nitrogen 573° C. and in air 544° C.
Molecular Structure:

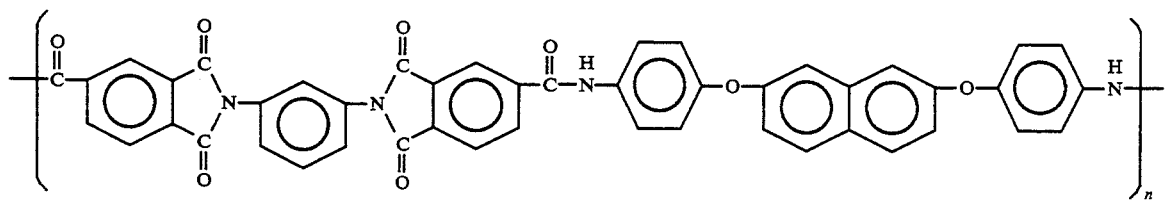

as follows:

The copoly(amide-imide )(2,3 ) can be prepared as

| Breaking Strength | Elongation at Break | Initial Modulus |
|---|---|---|
| 96 MPa | 8% | 1.82 GPa |

Molecular Structure:

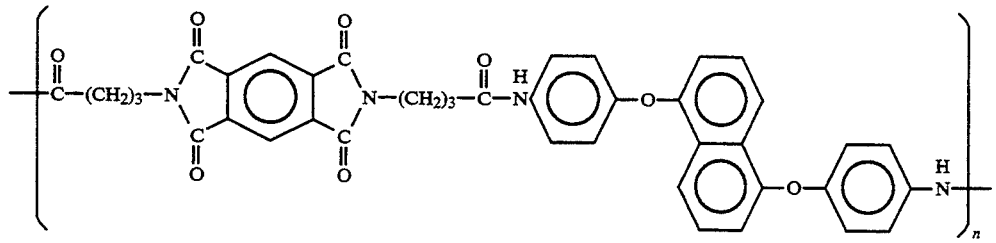

If we replace the 4-aminobutanoic acid by the 6-aminocaproic acid, we can quantitatively get the copoly(amide-imide) having an inherent viscosity of 0.94 dl/g.

The copoly(amide-imide)(2,7) can be prepared as follows:

After we stir to dissolve 0.02 mole m-phenylenediamine and 0.04 mole trimellitic anhydride in 40 ml N,N- follows:

Following the preparing procedures for the preceding copoly(amide-imide)(2,7), we can obtain the bis(N.N-trimellitoyl)-3.3'-dichloro-4.4'-diaminophenylmethane, by adding 20 mmole MOCA and 40 mmole trimellitic anhydride (TMA) in 300 ml flask. If we add 1.25 mmole such bis(N,N-trimellitoyl)-3,3'-4,4'- diaminophenylmethane, 1.25 mmole 2,3-bis(4-aminophenoxy)naphthalene, 0.4 g calcium chloride, 5 ml NMP, 1.2 ml pyridine and 0.8 ml triphenyl phosphite (TPP) in the 50 ml flask which is to react for 3 hours under an oil bath at 100 C. and supplemented with 6 ml NMP in the process of the increasing viscosity of the solution. After the solution is fully dipped in and washed by the methyl alcohol, we can get 1.19g slightly yellow copolymer (yield 100%) which, when measured in DMAc, exhibits an inherent viscosity 1.20 dl/g and has physical properties as follows:

| Mechanical properties: | | |
|---|---|---|
| Breaking Strength | Elongation at Break | Initial Modulus |
| 88 Mpa | 7% | 1.8 Gpa |
| Molecular Structure: | | |

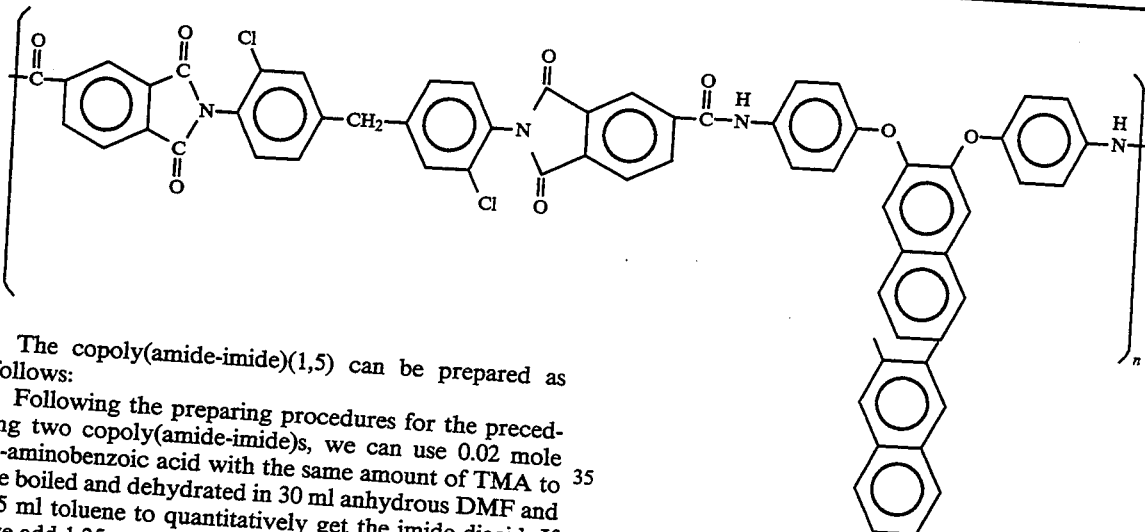

The copoly(amide-imide)(1,5) can be prepared as follows:

Following the preparing procedures for the preceding two copoly(amide-imide)s, we can use 0.02 mole p-aminobenzoic acid with the same amount of TMA to be boiled and dehydrated in 30 ml anhydrous DMF and 15 ml toluene to quantitatively get the imide-diacid. If we add 1.25 mmole such dicarboxylic acid, 1.25 mmole 1,5-bis(4-aminophenoxy)naphthalene, 0.8g calcium chloride, 5 ml NMP, 1.5 ml pyridine and 0.8 ml TPP to stirredly react in 50 ml flask at 100° C. for 3 hours, we can release from the methyl alcohol 0.82 g polymer which, when measured in DMAc, exhibits an inherent viscosity 1.00 dl/g and when casted from DMAc to form into the thin film has mechanical properties as follows:

| Breaking Strength | Elongation at Break | Initial Modulus |
|---|---|---|
| 105 Mpa | 7% | 2.2 Gpa |
| Molecular Structure: | | |

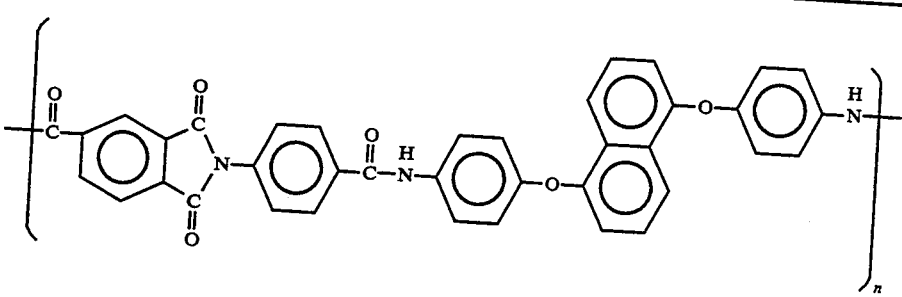

What we claim is:

1. A bis(4-aminophenoxy)naphthalene compound having the following structure:

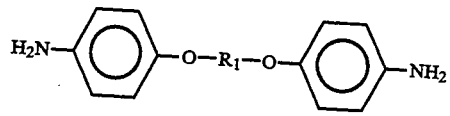

wherein $R_1$ is

2. A polymer polymerized from a monomer of said compound as claimed in claim 1 having the following structure:

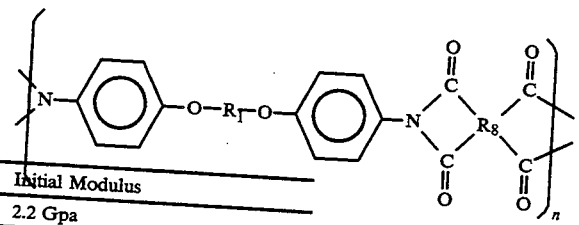

wherein said n is an integral number ranging from 5 to 500 and said $R_8$ is selected from a group consisting of

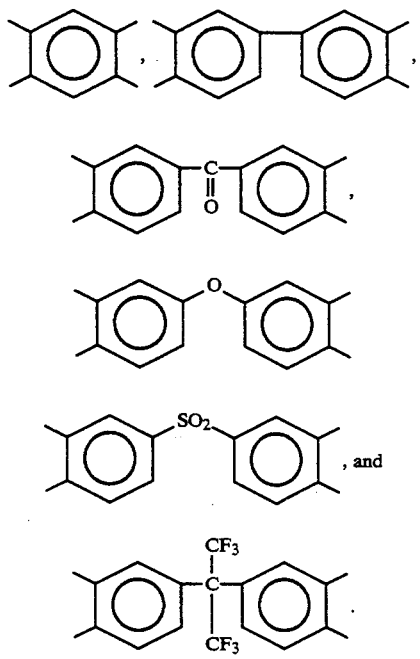

3. A polymer polymerized from a monomer of said compound as claimed in claim 1 having the following structure:

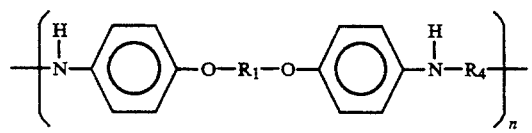

wherein said R₄ is selected from the group consisting of

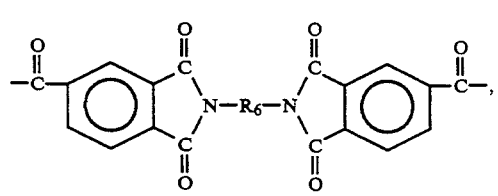

wherein said R₅ is selected from a group consisting of

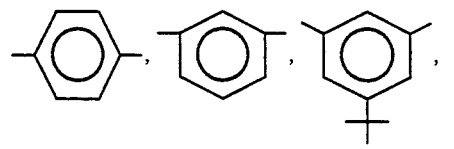

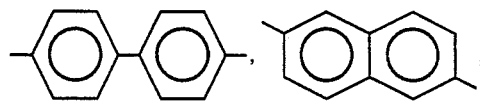

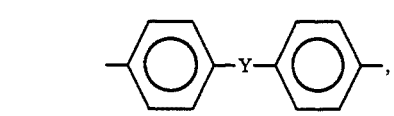

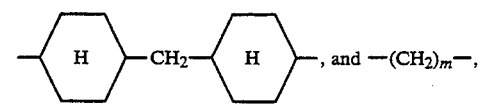

wherein said Y is one selected from a group consisting of SO₂, (CH₃)₂C<, and (CF₃)₂C<, and said m is an even number ranging from 2 to 12; said R₆ is selected from the group consisting of

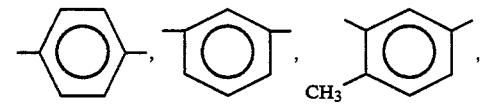

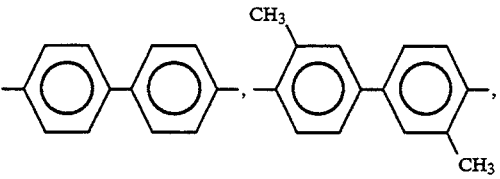

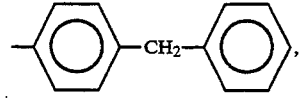

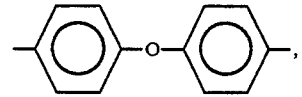

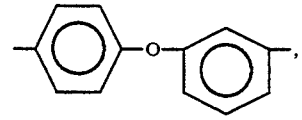

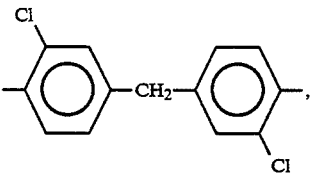

-continued
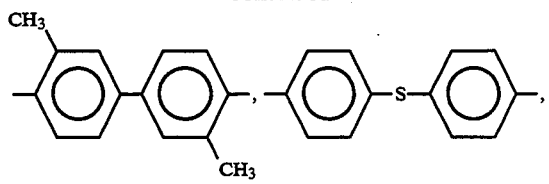
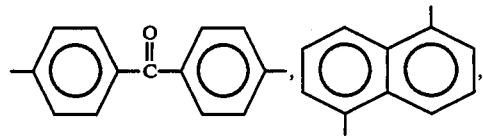
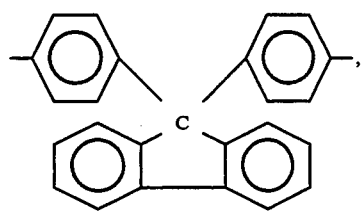
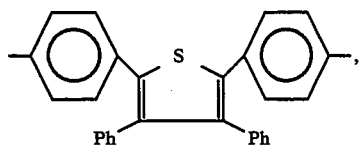
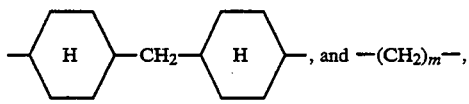
wherein said m is an integral number ranging from 2 to 12; said $R_7$ is selected from the group consisting of
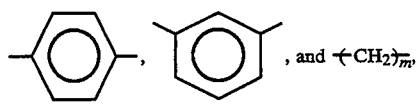
wherein said m is an integral number selected from a group consisting of 1, 2, 3, 4, 5, 10 and 11; and said $R_8$ is selected from a group consisting of
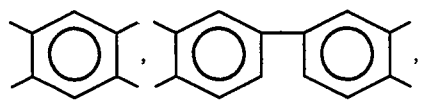
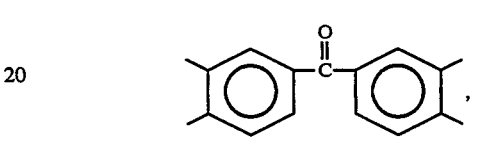
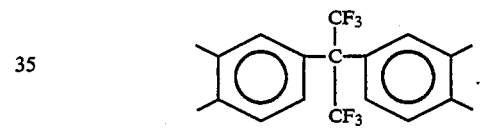
* * * * *